(12) United States Patent
Ellenbecker

(10) Patent No.: US 6,309,218 B1
(45) Date of Patent: Oct. 30, 2001

(54) APPARATUS FOR APPLYING SUCTION ADJACENT TO A TOOTH

(76) Inventor: John R. Ellenbecker, 2211 N. Jordan Ave., Juneau, AK (US) 99801

( * ) Notice: Subject to any disclaimer, the term of this patent is extended or adjusted under 35 U.S.C. 154(b) by 0 days.

(21) Appl. No.: 09/712,520

(22) Filed: Nov. 14, 2000

(51) Int. Cl.[7] .................................................. A61C 17/06
(52) U.S. Cl. ............................ 433/93; 433/138; 600/238
(58) Field of Search .................................. 433/93, 91, 94, 433/96, 140, 136, 138; 600/238, 237

(56) References Cited

U.S. PATENT DOCUMENTS

| D. 244,377 | 5/1977 | Sturdivant ................................ D24/8 |
| 1,010,146 | 11/1911 | Ivory . |
| 1,742,080 | 12/1929 | Jones . |
| 2,644,234 | 7/1953 | Scott . |
| 2,791,030 | 5/1957 | Tofflemire . |
| 2,811,777 | 11/1957 | Tofflemire . |
| 2,844,873 | * 7/1958 | Bober ...................................... 433/94 |
| 2,885,783 | 5/1959 | Golden . |
| 3,101,543 | 8/1963 | Baughan . |
| 5,071,347 | 12/1991 | Mcguire ................................. 433/97 |
| 5,203,699 | 4/1993 | Mcguire ................................. 433/94 |
| 5,800,173 | 9/1998 | Heasley ................................. 433/138 |

* cited by examiner

Primary Examiner—John J. Wilson
Assistant Examiner—Melba Bumgarner

(57) ABSTRACT

An apparatus for applying suction adjacent to a tooth for removing saliva from the operative area that includes a bow member for extending about a portion of a tooth of a patient that is substantially U-shaped with a central axis. The bow member includes a transverse portion that extends transverse to the central axis of the bow member and a pair of side portions each being for extending adjacent to lateral surfaces of the tooth. The side portions extend substantially parallel to the central axis, with each of the side portions having a root end connected to the transverse portion and a free end opposite the root end. The side portions of the bow member are resiliently flexible to permit spreading of the side portions. A pair of suction pads are each positionable adjacent to one of the lateral sides of the tooth and mountable adjacent to a lower surface of one of the side portions of the bow member. Each of the suction pads has a proximal and a distal end, with a bore being formed in the proximal end of each of the suction pads and extending toward the distal end of the suction pad. The device also includes a pair of suction conduits each being adapted for suctioning fluid from one of the suction pads. Each of the suction conduits extends into one of the suction pads through the bore in the suction pad. The suction conduits each have a lumen that extends along their length, and a plurality of apertures extend through the suction conduit for permitting fluid communication between the lumen and an exterior of the suction conduit.

16 Claims, 4 Drawing Sheets

APPARATUS FOR APPLYING SUCTION ADJACENT TO A TOOTH

BACKGROUND OF THE INVENTION

1. Field of the Invention

The present invention relates to dental suction devices and more particularly pertains to a new apparatus for applying suction adjacent to a tooth for removing saliva from the operative area.

2. Description of the Prior Art

Various dental procedures require that the tooth being operated upon be maintained in a relatively dry condition during procedures such as adhesive composite restorations and applications of occusal sealants. The surfaces of the operative tooth must be isolated from moisture (e.g., saliva) so that the bonding of such adhesives or sealers are not negatively affected by the moisture. Dental dams have been used to isolate an individual tooth or a plurality of teeth from moisture, but can be difficult or painful to use on teeth that have not completely erupted from the gum of the patient. Unfortunately, dental sealants are preferably applied to a tooth prior to the complete eruption of the tooth for the most effective protection of the tooth, and this makes use of the dental dam for applications of these protective sealants difficult.

Known prior art includes U.S. Pat. No. 5,800,173 to Heasley, which proposes an absorbent roll holder that does not actively remove saliva absorbed by the absorbent rolls, so repeated removal and replacement of the absorbent rolls may be necessary, especially during the performance of lengthy dental procedures (such as when used on multiple quadrants of the mouth), and thus interferes with the normal continuity of the procedure. Further, since the Heasley teaching contemplates removal and replacement of the absorbent rolls while the holder is in the mouth of the patient and during the procedure, the Heasley disclosure recommends that the absorbent roll mounting shafts have their free ends directed anteriorly in the mouth of the patient to reduce the possibility of the absorbent roll accidentally entering the throat of the patient during removal and replacement. Following this recommendation makes it difficult, if not impossible, for example, to use the Heasley device for applying a sealant to a partially erupted rearmost tooth (e.g., the first or second adult molar). Clamping of the Heasley device on a partially erupted first or second adult molar is not possible in order to direct the roll mounting shafts in an anterior direction as is recommended, and a patient will not have an erupted tooth located posterior of the partially erupted first or second adult molar.

No known dental device permits the isolation of a partially erupted rearmost tooth without imposing pain or discomfort on the patient. However, the partially erupted stage of the development of the first and second molars is the most effective time for applying dental sealants to the molars of children to prevent decay, and therefore the avoidance of discomfort in the patient is important.

The apparatus for applying suction adjacent to a tooth according to the present invention substantially departs from the conventional concepts and designs of the prior art.

SUMMARY OF THE INVENTION

In view of the foregoing disadvantages inherent in the known types of dental suction devices now present in the prior art, the present invention provides a new apparatus for applying suction adjacent to a tooth wherein the same can be utilized for removing saliva from the operative area.

The device of the present invention generally comprises a bow member for extending about a portion of a tooth of a patient. The bow member is substantially U-shaped with a central axis. The bow member includes a transverse portion for extending above a portion of the arcuate line of teeth, and the transverse portion extends transverse to the central axis of the bow member. The bow member also includes a pair of side portions each being for extending adjacent to lateral surfaces of the tooth. The side portions extend substantially parallel to the central axis of the bow member, with each of the side portions having a root end connected to the transverse portion and a free end opposite the root end. The side portions of the bow member are resiliently flexible to permit spreading of the side portions. The device includes a pair of suction pads each being adapted for positioning adjacent to one of the lateral sides of the anchor tooth and the focus tooth. Each of the suction pads is mounted adjacent to a lower surface of one of the side portions of the bow member. Each of the suction pads has a proximal and a distal end, with a bore being formed in the proximal end of each of the suction pads and extending toward the distal end of the suction pad. The device also includes a pair of suction conduits each being adapted for suctioning fluid from one of the suction pads. Each of the suction conduits extends into one of the suction pads through the bore in the suction pad. Each of the suction conduits has a lumen that extends along the length of the suction conduit. Each of the suction conduits has a plurality of apertures through the suction conduit for permitting fluid communication between the lumen and an exterior of the suction conduit.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
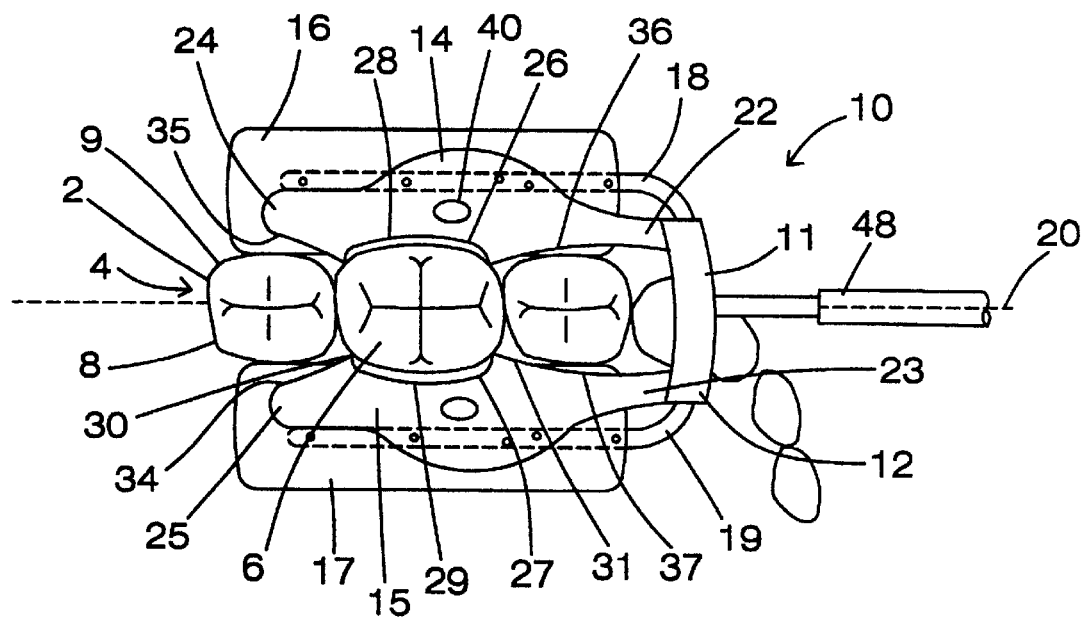
FIG. 1 is a schematic top view of a new apparatus for applying suction adjacent to a tooth according to the present invention.
Figure 2:
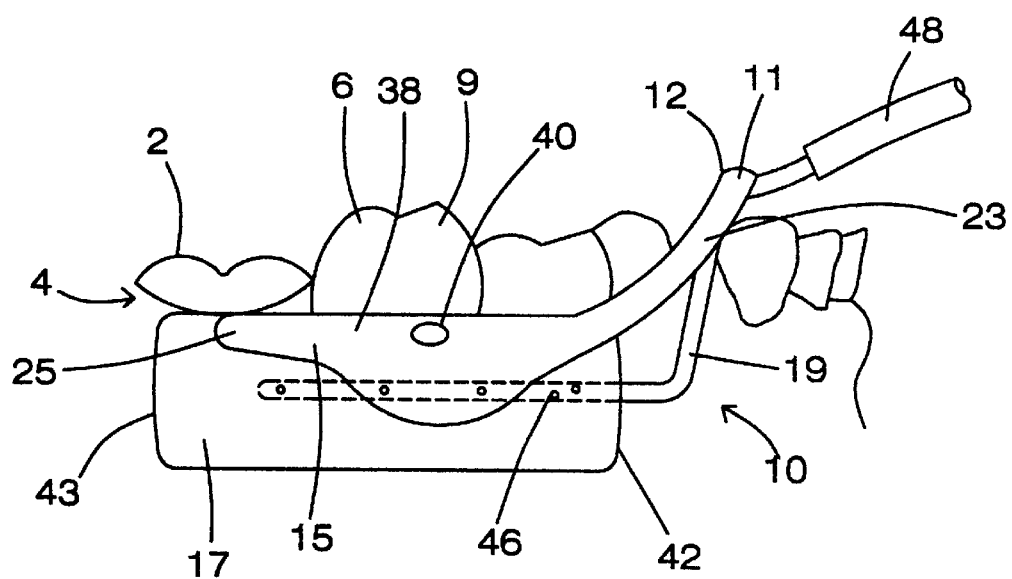
FIG. 2 is a schematic side view of the present invention employed on the mandibular arch (lower jaw) of a patient.
Figure 3:
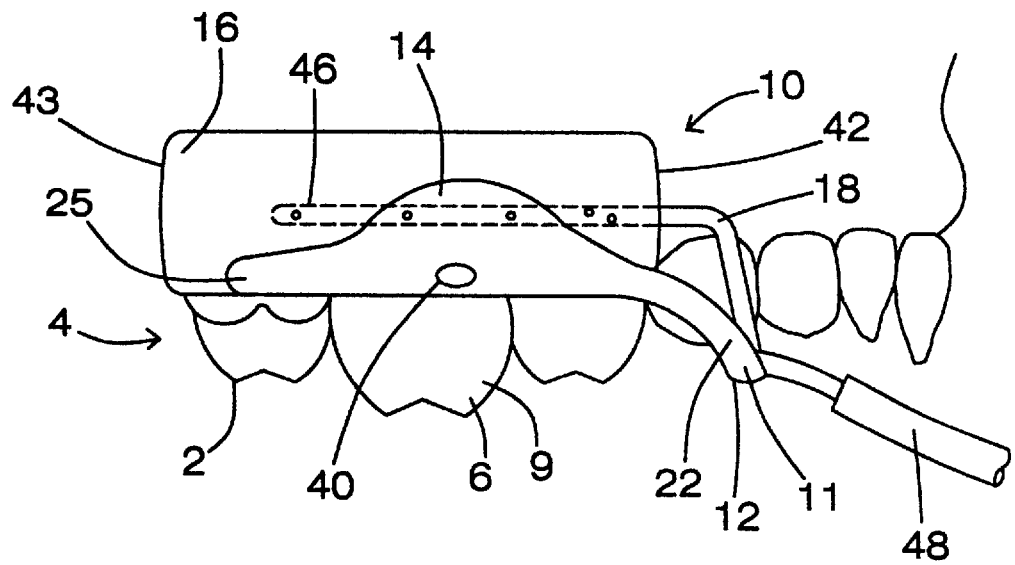
FIG. 3 is a schematic side view of the present invention employed on the maxillary arch (upper jaw) of the patient.
Figure 4:
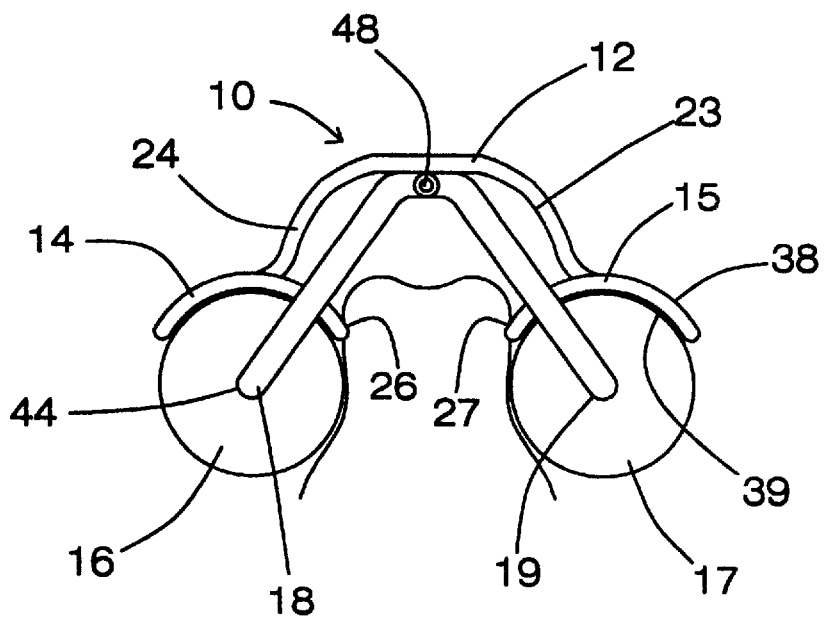
FIG. 4 is a schematic end view of the present invention.
Figure 5:
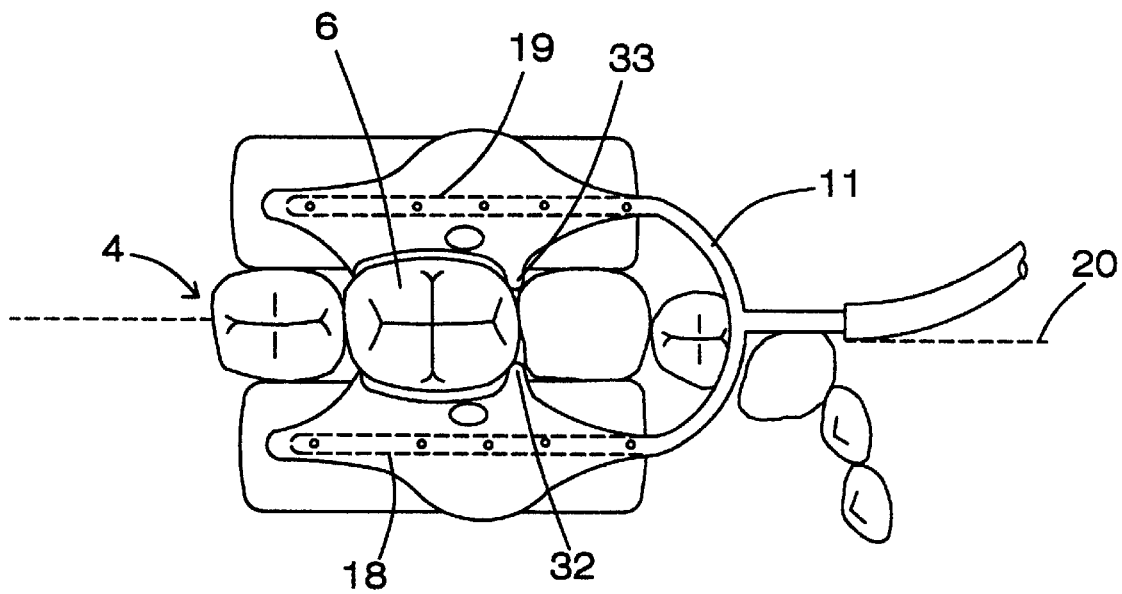
FIG. 5 is a schematic top view of the present invention with an optional variation.
Figure 6:
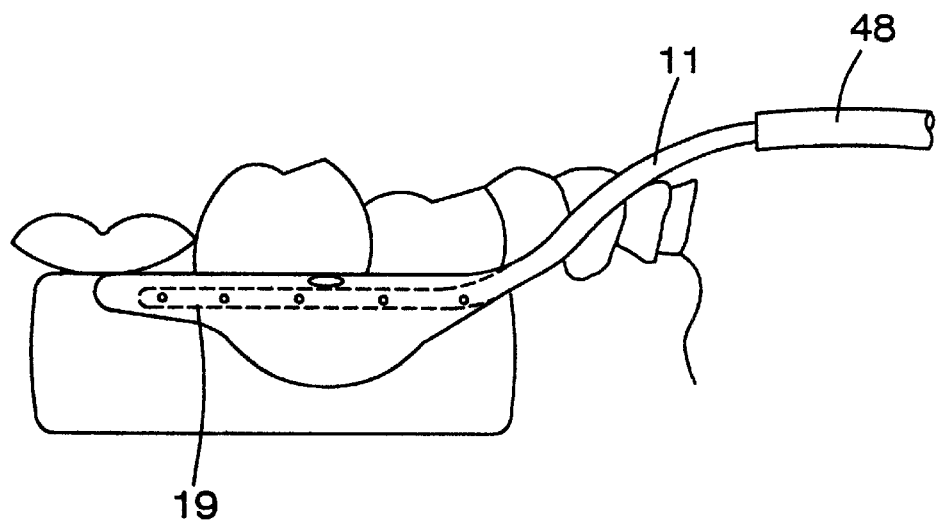
FIG. 6 is a schematic side view of the optional variation of FIG. 5.
Figure 7:
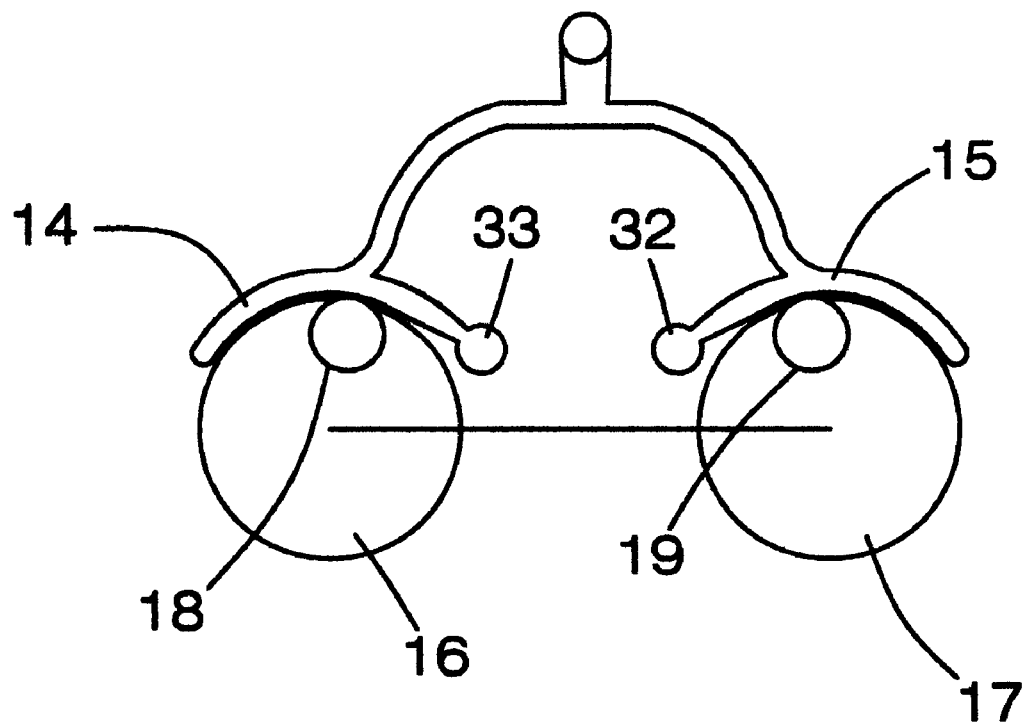
FIG. 7 is a schematic end view of the optional variation of FIG. 5.

With reference now to the drawings, and in particular to FIGS. 1 through 7 thereof, a new apparatus for applying suction adjacent to a tooth embodying the principles and concepts of the present invention and generally designated by the reference numeral 10 will be described.

The invention includes a device for facilitating isolation or shielding of a focus tooth 2 of a patient from saliva during dental procedures. Illustratively, the focus tooth 2 is one of a plurality of teeth oriented in an arcuate line 4 in a patient's mouth, such as in the maxillary or the mandibular arch. At least one anchor tooth 6 in the arcuate line is located adjacent to the focus tooth 2. Each of the teeth has an inner lateral surface 8 facing inwardly from the arcuate line and each tooth has an outer lateral surface 9 facing outwardly from the arcuate line.

The device 10 for applying suction adjacent to a tooth generally includes a bow member 11 comprising a transverse portion 12 and a pair of side portions 14, 15 which extend from the transverse portion, a suction pad 16, 17 mounted on each side portion of the bow member, and a suction conduit 18, 19 extending into each of the suction pads.

The bow member 11 of the invention is provided for extending about a portion of a focus tooth 2 of a patient. The bow member 11 is preferably substantially U-shaped for engaging the inner and outer lateral surfaces of the teeth in the arch. The bow member 11 has a central axis 20. The transverse portion 12 of the bow member is adapted for extending above a portion of the arcuate line 4 of teeth. The transverse portion 12 extends transverse to the central axis 20 of the bow member.

The pair of side portions 14, 15 of the bow member are each provided for extending adjacent to one of the lateral surfaces of the tooth. The side portions 14, 15 extend substantially parallel to the central axis 20 of the bow member. The side portions extend from the transverse portion 12 preferably in a substantially parallel relationship to each other, and both of the side portions also preferably extend substantially perpendicular to the transverse portion of the bow member. Each of the side portions has a root end 22, 23 that is connected to the transverse portion and a free end 24, 25 located opposite the root end. The side portions of the bow member are resiliently flexible in an outward direction to permit the side portions to be spread away from each other for positioning a tooth therebetween such that release of the side portions can engage the lateral surfaces of the tooth.

Each of the side portions 14, 15 has a tooth gripping structure for gripping one of the lateral surfaces of the anchor tooth of the patient. Each of the tooth gripping structures includes an inward surface 26, 27 on each of the side portions 14, 15. Each inward surface 26, 27 is oriented toward the central axis 20 of the bow member and toward the inward surface of the other of the side portions.

Each of the inward surfaces 26, 27 has a central section 28, 29 oriented in substantial opposition to the central section of the inward surface of the other of the side portions. Each of the central sections is concave in shape for extending about, or embracing, a portion of a lateral surface of the anchor tooth. The central concave section 28, 29 of one of the side portions is positioned in opposition to the central concave section of the other of the side portions. Optionally, each of the central sections of the inward surfaces may be provided with a beveled profile such that the thickness of the inward surfaces tapers relatively thinner toward the surface of the tooth.

The central concave section 28, 29 of each inward surface extends between protruding points 30, 31 of the inward surface. The protruding points 30, 31 on the inward surface extend inwardly toward the protruding points of the other of the side portions. In a highly preferred embodiment, at least one of the protruding points of each of the side portions has an interproximal ball 32, 33 mounted thereon for engaging an undercut surface of a lateral surface of one or more of the teeth. The interproximal ball 32, 33 of one of the side portions is positioned laterally opposite of the interproximal ball of the other of the side portions.

The inward surface 26, 27 of each of the side portions may have a first end section 34, 35 extending from the central concave section 28, 29 toward the free end 24, 25 of the side portion. The first end section of the inward surface extends generally away from the central axis of the bow member. The first end section 34, 35 is arcuate for extending about a portion of the lateral surface of the focus tooth located adjacent to the anchor tooth. Preferably, the first end section does not even touch the tooth. The first end section of one of the side portions is positioned in opposition to the first end section of the other of the side portions.

The inward surface of each of the side portions may also have a second end section 36, 37 extending from the central concave section toward the root end 22, 23 of the side portion. The second end section of the inward surface extends generally away from the central axis of the bow member. The second end section 36, 37 is arcuate for extending about a portion of the lateral surface of the tooth located adjacent to the anchor tooth and opposite the focus tooth in the arcuate line of teeth of the patent's mouth. The second end section of one of the side portions is positioned in opposition to the second end section of the other of the side portions.

Each of the side portions 14, 15 of the bow member has an upper surface 38 and a lower surface 39. Preferably the lower surface is concave for abutting and fitting against the suction pad and the upper surface of each side portion is convex. Preferably, each of the side portions 14, 15 has a hole 40 for being engaged by a clamp forceps so that the clamp forceps may be used to spread the side portions of the resiliently flexible bow member. The hole 40 is preferably located substantially centrally between the root 22, 23 and free 24, 25 ends of each of the side portions 14, 15. In the most preferred embodiment, the side portions of the bow member lie substantially in a common plane and the transverse portion lies in a plane that is parallel to and above the plane defined by the side portions for bridging over the arcuate line of teeth.

The pair of suction pads 16, 17 are each provided for positioning adjacent to one of the lateral sides of the focus tooth and preferably the anchor tooth. Each of the suction pads is mounted adjacent to the lower surface 39 of one of the side portions of the bow member. Each of the suction pads has a proximal 42 and a distal 43 end. A bore 44 is formed in the proximal end of each of the suction pads and extends longitudinally toward the distal end of the suction pad, but preferably does not reach the distal end. Each of the suction pads may have a substantially cylindrical exterior shape. Most preferably the suctions pads are formed from an open cell foamed material for facilitating the flow of fluid therethrough to the suction conduits. Optionally, and less preferably, cotton may be used as the material forming the suctions pads.

Each of the pair of suction conduits 18, 19 is provided for suctioning fluid from one of the suction pads. Each of the suction conduits extends into one of the suction pads through the bore 44 in the suction pad. Each of the suction conduits 18, 19 has a lumen extending along the length of the suction conduit, and has a plurality of apertures 46 through the wall of the suction conduit for permitting fluid communication between the lumen and an exterior of the suction conduit. The pair of suction conduits is joined together to form a suction tube 48. The suction tube 48 is adapted for connecting to a conventional dental suction source (not shown) for drawing fluids through the suction pads and through the suction conduits away from the mouth of the patient.

Each of the suction conduits is positioned at a spacing from the lower surface of the side member such that a portion of the suction pad may be located between the suction conduit and the side portion for placing the suction conduit toward a center of the suction pad (see FIGS. 1 through 4). Optionally, each of the suction conduits may be attached to the lower surface of one of the side members (see FIGS. 5 through 7). Preferably, the suction conduit is positioned about midway between lateral edges of the side portions on the lower surface. The attached suction conduit and side portion may be formed integrally to each other as a single piece, which is especially useful when the assembly is designed for a one-time use and is constructed from a disposable material (such as a form of plastic).

Illustratively, the suction conduits may be formed of tubing having an inside diameter of approximately ⅛-inch, and may be formed of stainless steel in the reusable devices.

In use, a suction pad is mounted on each of the suction conduits of the device by inserting each suction conduit into the bore in the suction pad. The side portions of the bow member are incrementally spread apart so that the anchor tooth may be inserted in between the side portions of the bow member with the central concave sections of the inward surfaces of the side members engaging the lateral surfaces of the anchor tooth. Illustratively, the application of a dental sealant to the partially erupted second adult molar (as the focus tooth) involves engaging the first adult molar as the anchor tooth. Suction is applied to the suction tube and conduits so that saliva and other fluids absorbed by the suction pads are drawn through the apertures in the suction conduit.

Illustratively, the suction pads may be provided in a variety of sizes, such as, for example, an extra small pad having a length of approximately 1.25 inches long (from proximal to distal ends) and a diameter of approximately 5/16 inch, a small pad having a length of approximately 1.5 inches and a diameter of approximately ⅜ inch, a medium pad having a length of approximately 1.75 inches and a diameter of approximately 7/16 inch, and a large pad having a length of approximately of 2 inches and a diameter of approximately ½ inch. For example, one of the relatively smaller sized devices may be used for clamping the second primary molar when sealing (or otherwise operating on) the first adult molar, and a relatively larger size may be used for clamping the first adult molar when sealing (or otherwise operating on) the second adult molar.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A device for isolating a focus tooth of a patient from saliva during dental procedures, the focus tooth being one of a plurality of teeth oriented in an arcuate line in a patient's mouth, at least one anchor tooth in the arcuate line being located adjacent to the focus tooth, each of the teeth having an inner lateral surface facing inwardly from the arcuate line and an outer lateral surface facing outwardly from the arcuate line, the device comprising:

a bow member for extending about a portion of a tooth of a patient, the bow member being substantially U-shaped, the bow member having a central axis, the bow member including:

a transverse portion for extending above a portion of the arcuate line of teeth, the transverse portion extending transverse to the central axis of the bow member; and a pair of side portions each being for extending adjacent to lateral surfaces of the tooth, the side portions extending substantially parallel to the central axis of the bow member, each of the side portions having a root end connected to the transverse portion and a free end opposite the root end, the side portions of the bow member being resiliently flexible;

a pair of suction pads each being adapted for positioning adjacent to one of the lateral sides of the anchor tooth and the focus tooth, each of the suction pads being mounted adjacent to a lower surface of one of the side portions of the bow member, each of the suction pads having a proximal and a distal end, a bore being formed in the proximal end of each of the suction pads and extending toward the distal end of the suction pad; and a pair of suction conduits each being adapted for suctioning fluid from one of the suction pads, each of the suction conduits extending into one of the suction pads through the bore in the suction pad, each of the suction conduits having a lumen extending along the length of the suction conduit, each of the suction conduits having a plurality of apertures through the suction conduit for permitting fluid communication between the lumen and an exterior of the suction conduit.

2. The device of claim 1 wherein the side portions extend from the transverse portion in a substantially parallel relationship, each of the side portions extending substantially perpendicular to the transverse portion of the bow member.

3. The device of claim 1 wherein each of the side portions has a tooth gripping structure for gripping one of the lateral surfaces of the anchor tooth of the patient, each of the tooth gripping structures including an inward surface on one of the side portions, each inward surface of the side portions being oriented toward the central axis of the bow member and the inward surface of the other of the side portions.

4. The device of claim 3 wherein each of the inward surfaces has a central section oriented in substantial opposition to the central section of the inward surface of the other of the side portions, each of the central sections being concave, the central concave section of one of the side portions being opposed to the central concave section of the other of the side portions.

5. The device of claim 4 wherein the central concave section of each inward surface extends between protruding points, the protruding points on the inward surface extending inwardly toward the protruding points of the other of the side portions.

6. The device of claim 5 wherein at least one of the protruding points of each of the side portions has an interproximal ball mounted thereon for engaging an undercut surface of a tooth, the interproximal ball of each side portion being positioned laterally opposite of the interproximal ball of the other of the side portions.

7. The device of claim 4 wherein the inward surface of each of the side portions has a first end section extending from the central concave section toward the free end of the side portion, the first end section of the inward surface extending generally away from the central axis of the bow member, the first end section being arcuate for extending about a portion of the lateral surface of the focus tooth located adjacent to the anchor tooth, the first end section of one of the side portions being opposed to the first end section of the other of the side portions.

8. The device of claim 4 wherein the inward surface of each of the side portions has a second end section extending from the central concave section toward the root end of the side portion, the second end section of the inward surface extending generally away from the central axis of the bow member, the second end section being arcuate for extending about a portion of the lateral surface of the tooth located adjacent to the anchor tooth and opposite the focus tooth in the arcuate line of teeth of the patent's mouth, the second end section of one of the side portions being opposed to the second end section of the other of the side portions.

9. The device of claim 1 wherein each of the side portions has an upper surface and a lower surface, the lower surface being concave and the upper surface being convex.

10. The device of claim 1 wherein each of the side portions has a hole for being engaged by a clamp forceps, the aperture being located substantially centrally between the root and free ends of the side portion.

11. The device of claim 1 wherein the side portions of the bow member lie substantially in a common plane, the transverse portion extending in a plane parallel to the plane of the side portions, the plane of the transverse portion being located above the plane of the side portions.

12. The device of claim 1 wherein each of the suction pads has a substantially cylindrical exterior shape.

13. The device of claim 1 wherein the pair of suction conduits are joined together to form a suction tube, the suction tube being adapted for connecting to a suction source.

14. The device of claim 1 wherein each of the suction conduits is spaced from the lower surface of the side portion for permitting positioning a portion of the suction pad between the suction conduit and the side portion for placing the suction conduit toward a center of the suction pad.

15. The device of claim 1 wherein each of the suction conduits is attached to the lower surface of one of the side portions, the suction conduit being positioned between lateral edges of the side portions.

16. A device for isolating a focus tooth of a patient from saliva during dental procedures, the focus tooth being one of a plurality of teeth oriented in an arcuate line in a patient's mouth, at least one anchor tooth in the arcuate line being located adjacent to the focus tooth, each of the teeth having an inner lateral surface facing inwardly from the arcuate line and an outer lateral surface facing outwardly from the arcuate line, the device comprising:

a bow member for extending about a tooth of a patient, the bow member being substantially U-shaped, the bow member having a central axis, the bow member including:

a transverse portion for extending above a portion of the arcuate line of teeth, the transverse portion extending transverse to the central axis of the bow member; and a pair of side portions each being for extending adjacent to lateral surfaces of the tooth, the side portions extending substantially parallel to the central axis of the bow member, the side portions extending from the transverse portion in a substantially parallel relationship, each of the side portions extending substantially perpendicular to the transverse portion of the bow member each of the side portions having a root end connected to the transverse portion and a free end opposite the root end, the side portions of the bow member being resiliently flexible;

each of the side portions having a tooth gripping structure for gripping one of the lateral surfaces of the anchor tooth of the patient, each of the tooth gripping structures including an inward surface on one of the side portions, each inward surface of the side portions being oriented toward the central axis of the bow member and the inward surface of the other of the side portions;

each of the inward surfaces having a central section oriented in substantial opposition to the central section of the inward surface of the other of the side portions, each of the central sections being concave, the central concave section of one of the side portions being opposed to the central concave section of the other of the side portions;

wherein the central concave section of each inward surface extends between protruding points, the protruding points on the inward surface extending inwardly toward the protruding points of the other of the side portions;

at least one of the protruding points of each of the side portions having an interproximal ball mounted thereon for engaging an undercut surface of a tooth, the interproximal ball of each side portion being positioned laterally opposite of the interproximal ball of the other of the side portions;

the inward surface of each of the side portions having a first end section extending from the central concave section toward the free end of the side portion, the first end section of the inward surface extending generally away from the central axis of the bow member, the first end section being arcuate for extending about a portion of the lateral surface of the focus tooth located adjacent to the anchor tooth, the first end section of one of the side portions being opposed to the first end section of the other of the side portions;

the inward surface of each of the side portions having a second end section extending from the central concave section toward the root end of the side portion, the second end section of the inward surface extending generally away from the central axis of the bow member, the second end section being arcuate for extending about a portion of the lateral surface of the tooth located adjacent to the anchor tooth and opposite the focus tooth in the arcuate line of teeth of the patent's mouth, the second end section of one of the side portions being opposed to the second end section of the other of the side portions;

wherein each of the side portions has an upper surface and a lower surface, the lower surface being concave and the upper surface being convex, wherein each of the side portions has a hole for being engaged by a clamp forceps, the aperture being located substantially centrally between the root and free ends of the side portion;

wherein the side portions of the bow member lie substantially in a common plane, the transverse portion extending in a plane parallel to the plane of the side portions, the plane of the transverse portion being located above the plane of the side portions;

a pair of suction pads each being adapted for positioning adjacent to one of the lateral sides of the anchor tooth and the focus tooth, each of the suction pads being mounted adjacent to the lower surface of one of the side portions of the bow member, each of the suction pads having a proximal and a distal end, a bore being formed in the proximal end of each of the suction members and extending toward the distal end of the suction member, each of the suction pads having a substantially cylindrical exterior shape, each of the suction pads being formed by an open cell foamed material permitting the flow of fluid therethrough;

a pair of suction conduits each being adapted for suctioning fluid from one of the suction pads, each of the suction conduits extending into one of the suction pads through the bore in the suction pad, each of the suction conduits having a lumen extending along the length of the suction conduit, each of the suction conduits having a plurality of apertures through the suction conduit for permitting fluid communication between the lumen and an exterior of the suction conduit, the pair of suction conduits being joined together to form a suction tube, the suction tube being adapted for connecting to a suction source, wherein each of the suction conduits is positioned at a spacing from the side portion for positioning a portion of the suction pad between the suction conduit and the side portion for placing the suction conduit toward a center of the suction pad.

\* \* \* \* \*